US012773098B2

(12) United States Patent
Kwon et al.

(10) Patent No.: US 12,773,098 B2
(45) Date of Patent: Oct. 27, 2026

(54) BUCKLING PREVENTION DEVICE FOR ENDOSCOPE OVERTUBE

(71) Applicants: KOREA ADVANCED INSTITUTE OF SCIENCE AND TECHNOLOGY, Daejeon (KR); ROEN Surgical, Inc., Daejeon (KR)

(72) Inventors: Dong Soo Kwon, Daejeon (KR); Deok Gyoon Chung, Daejeon (KR); Byung Sik Cheon, Daejeon (KR)

(73) Assignees: KOREA ADVANCED INSTITUTE OF SCIENCE AND TECHNOLOGY, Daejeon (KR); ROEN Surgical, Inc., Daejeon (KR)

( * ) Notice: Subject to any disclaimer, the term of this patent is extended or adjusted under 35 U.S.C. 154(b) by 654 days.

(21) Appl. No.: 18/013,885

(22) PCT Filed: Nov. 26, 2020

(86) PCT No.: PCT/KR2020/016958
§ 371 (c)(1),
(2) Date: Jan. 12, 2023

(87) PCT Pub. No.: WO2022/004968
PCT Pub. Date: Jan. 6, 2022

(65) Prior Publication Data

US 2024/0008715 A1 Jan. 11, 2024

(30) Foreign Application Priority Data

Jun. 30, 2020 (KR) ........................ 10-2020-0079879

(51) Int. Cl.
*A61B 1/00* (2006.01)
*A61B 1/005* (2006.01)

(52) U.S. Cl.
CPC ...... *A61B 1/00148* (2022.02); *A61B 1/00135* (2013.01); *A61B 1/00147* (2013.01); *A61B 1/00154* (2013.01); *A61B 1/0057* (2013.01)

(58) Field of Classification Search
CPC ............ A61B 1/00147; A61B 1/00149; A61B 1/00154; A61B 1/0014; A61B 1/00135; A61B 1/01
See application file for complete search history.

(56) References Cited

U.S. PATENT DOCUMENTS 5,514,074 A 5/1996 Yabe et al.
6,202,272 B1 3/2001 Jackson
(Continued)

FOREIGN PATENT DOCUMENTS

CN 103889348 6/2014
CN 204863076 12/2015
(Continued)

OTHER PUBLICATIONS

"International Search Report (Form PCT/ISA/210) of PCT/KR2020/016958," mailed on Mar. 29, 2021, with English translation thereof, pp. 1-4.

*Primary Examiner* — Ryan N Henderson
(74) *Attorney, Agent, or Firm* — JCIPRNET

(57) ABSTRACT

A buckling prevention device for an endoscope overtube according to an embodiment is a buckling prevention device for an endoscope overtube, which includes a plurality of supports capable of supporting an endoscope overtube and a base for supporting the plurality of supports. The plurality of supports includes: an endoscope support which is slidably connected to the base and can support an endoscope body; an overtube support which is fixed to a side of the base and supports an overtube connected to the endoscope body; and at least one additional support for supporting the overtube, the additional support being installed between the endoscope
(Continued)

support and the overtube support and slidably with respect to the base, wherein according to a sliding operation of the endoscope support, spacings between every pair of supports, which are most adjacent to each other, among the plurality of supports may have the same amount of change.

4 Claims, 6 Drawing Sheets

(56) References Cited

U.S. PATENT DOCUMENTS

| | | | | |
|---|---|---|---|---|
| 6,875,170 | B2 | 4/2005 | Francois et al. | |
| 10,059,011 | B2 | 8/2018 | Burlot | |
| 2005/0234293 | A1 * | 10/2005 | Yamamoto ............ | A61B 90/57 600/102 |
| 2007/0185485 | A1 | 8/2007 | Hauck et al. | |
| 2011/0144576 | A1 | 6/2011 | Rothe et al. | |

FOREIGN PATENT DOCUMENTS

| | | |
|---|---|---|
| CN | 106175652 | 12/2016 |
| JP | 2008229167 | 10/2008 |
| JP | 2009183602 | 8/2009 |
| JP | 3186191 | 9/2013 |
| KR | 100743612 | 8/2007 |
| KR | 20110020640 | 3/2011 |
| KR | 101744106 | 6/2017 |
| KR | 101777266 | 9/2017 |

* cited by examiner

BUCKLING PREVENTION DEVICE FOR ENDOSCOPE OVERTUBE

TECHNICAL FIELD

The following description relates to a buckling prevention device for an endoscope overtube.

BACKGROUND ART

To implement a motion of an endoscope as intended, it is necessary to manage the endoscope to prevent buckling of an overtube of the endoscope. If buckling of the overtube occurs, it is impossible to move the endoscope as intended. For example, when buckling occurs at the center of the overtube while a user is moving the overtube forward, the overtube may be deformed instead of moving forward. Thus, there is a demand for technology to effectively prevent buckling from occurring in the overtube.

The above description is information the inventor(s) acquired during the course of conceiving the present disclosure, or already possessed at the time, and is not necessarily art publicly known before the present application was filed.

DISCLOSURE OF THE INVENTION

Technical Goals

An aspect of an embodiment is to provide a buckling prevention device for an endoscope overtube.

Technical Solutions

A buckling prevention device for an endoscope overtube according to an embodiment is a buckling prevention device for an endoscope overtube, which includes a plurality of supports configured to support an endoscope overtube, and a base configured to support the plurality of supports. The plurality of supports includes an endoscope support slidably connected to the base and configured to support an endoscope body; an overtube support fixed to one side of the base and configured to support an overtube connected to the endoscope body; and at least one additional support configured to support the overtube, the at least one additional support being installed slidably with respect to the base, between the endoscope support and the overtube support. Variations in spacings between each pair of supports that are most adjacent to each other among the plurality of supports may be identical to each other, based on a sliding operation of the endoscope support.

The buckling prevention device may further include a wire fixed to each of the plurality of supports based on an arrangement order from the overtube support to the endoscope support, and the wire may be disposed to be bent a plurality of times from one end to another end.

The wire may include a plurality of elastic bodies configured to allow a total length of the wire to be changed based on a sliding distance of the endoscope support.

The elastic bodies may be configured to provide elastic forces in a direction in which the endoscope support moves away from the overtube support.

The buckling prevention device may further include a plurality of hook portions configured to maintain a bent shape of the wire.

At least a part of the plurality of hook portions may be a pulley.

The wire may include at least one elastic body disposed between each pair of supports that are most adjacent to each other among the plurality of supports. The at least one elastic body disposed between the each pair of the supports may have the same elastic modulus.

Each of the plurality of supports may include a fixing portion fixed to the wire, and the wire may be bent an even number of times between a pair of fixing portions that are most adjacent to each other based on a longitudinal direction of the wire.

At least one elastic body configured to allow a total length of the wire to be changed may be included in a portion of the wire between the pair of fixing portions.

The plurality of supports may each include a support hole through which the endoscope overtube passes.

The endoscope body may be detachable from the endoscope support.

A buckling prevention device for an endoscope overtube according to an embodiment is a buckling prevention device for an endoscope overtube, which includes a plurality of supports configured to support an endoscope overtube, and a base configured to support the plurality of supports. The plurality of supports includes a first support fixed to one side of the base and configured to support an overtube connected to an endoscope body; an endoscope support slidably connected to the base and configured to support the endoscope body; a second support configured to support the overtube, the second support being installed slidably with respect to the base, between the first support and the endoscope support; and a third support configured to support the overtube, the third support being installed slidably with respect to the base, between the second support and the endoscope support. A displacement amount by which the third support slides may be greater than a displacement amount by which second support slides, based on a sliding operation of the endoscope support.

Effects

A buckling prevention device for an endoscope overtube according to an embodiment may effectively prevent buckling from occurring in an overtube.

In addition, a buckling prevention device for an endoscope overtube according to an embodiment may be configured to have a compact length while ensuring a sufficient stroke length.

BEST MODE FOR CARRYING OUT THE INVENTION

Figure 1:
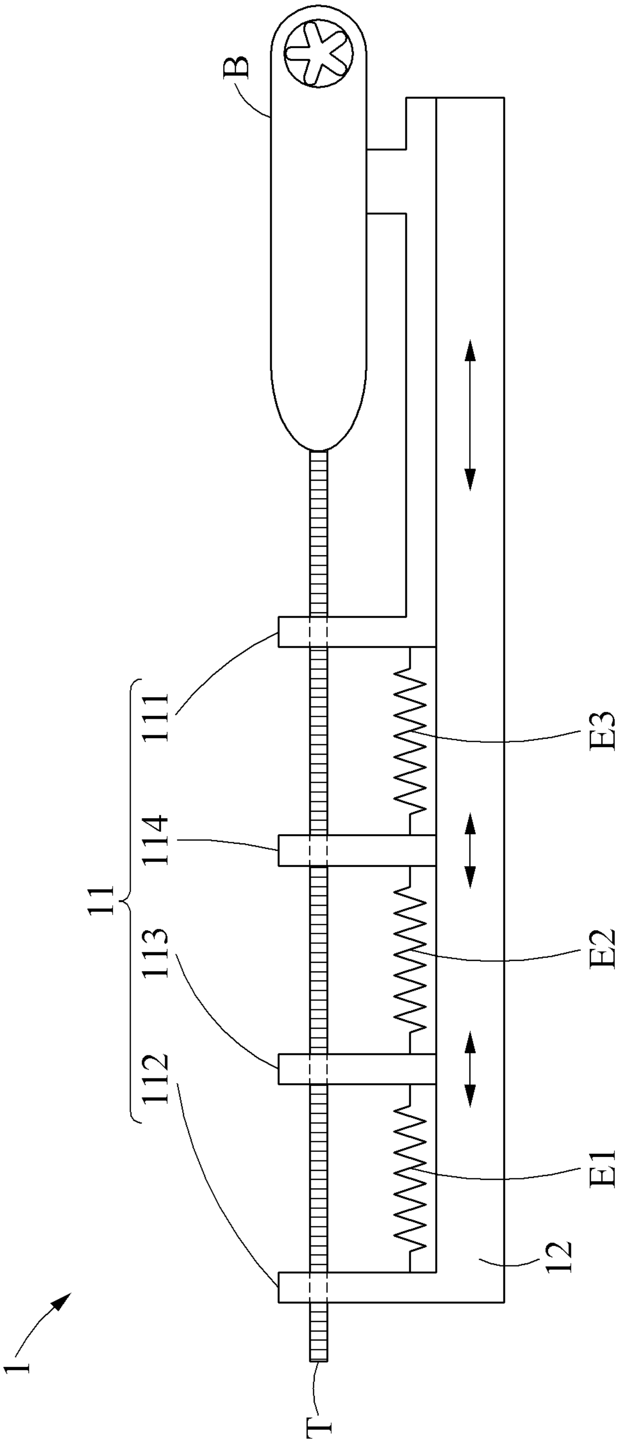
FIGS. 1 and 2 are diagrams illustrating an operation of a buckling prevention device for an endoscope overtube based on a change in a stroke distance of an endoscope, according to an embodiment.

Hereinafter, embodiments will be described in detail with reference to the accompanying drawings. When reference numerals refer to components of each drawing, it is noted that although the same components are illustrated in different drawings, the same components are designated by the same reference numerals as possible. In addition, in describing the embodiments, when it is determined that the detailed description of the known components and functions related to the present disclosure may obscure understanding of the embodiments, the detailed description thereof will be omitted.

Terms such as first, second, A, B, (a), (b), and the like may be used in describing the components of the embodiments. The terms are only used to distinguish a component from another component, but nature or an order of the component is not limited by the terms. It should be noted that if it is described in the specification that one component is "connected," "coupled" or "joined" to another component, the former may be directly "connected," "coupled," and "joined" to the latter or "connected", "coupled", and "joined" to the latter via another component.

A component, which has the same common function as a component included in one embodiment, will be described by using the same name in other embodiments. Unless disclosed to the contrary, the configuration disclosed in one embodiment may be applied to other embodiments, and the specific description of the repeated configuration will be omitted.

Figure 2:
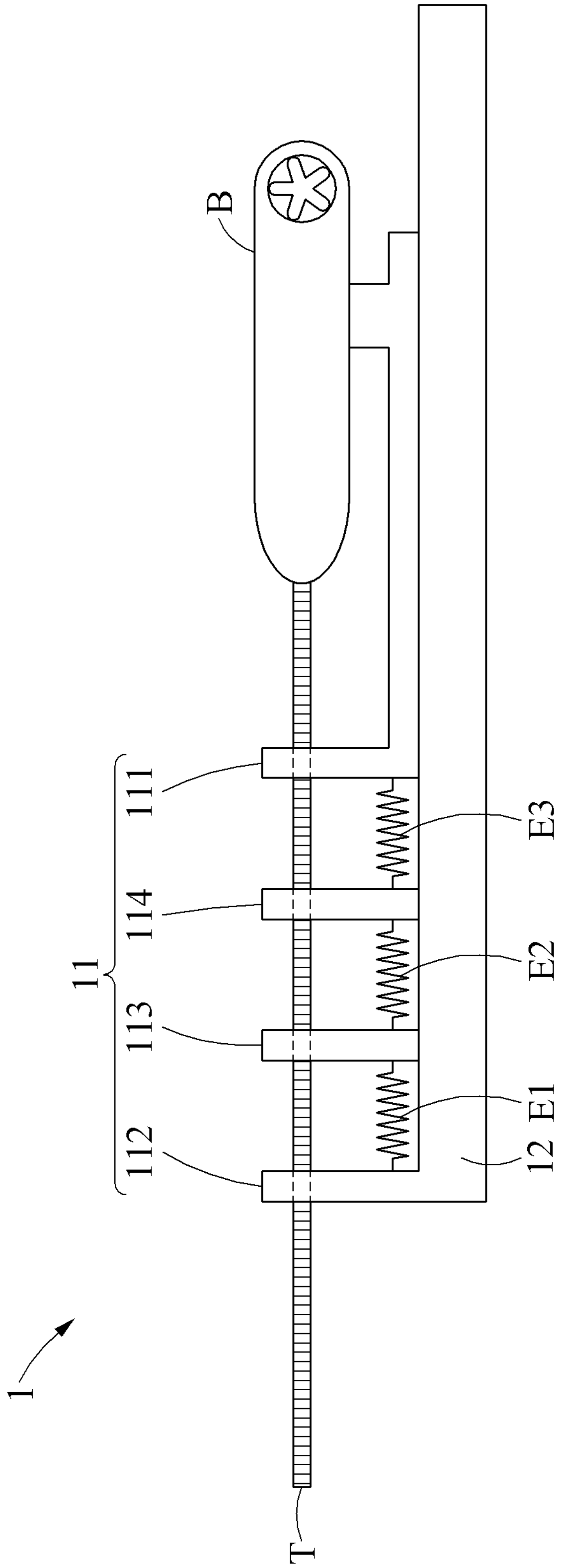

FIGS. 1 and 2 are diagrams illustrating an operation of a buckling prevention device for an endoscope overtube based on a change in a stroke distance of an endoscope, according to an embodiment.

Referring to FIGS. 1 and 2, a buckling prevention device 1 for an endoscope overtube (hereinafter, referred to as a "buckling prevention device 1") may prevent buckling of an overtube T by supporting a plurality of points in a longitudinal direction of the overtube T. The overtube T may be extended forward from an endoscope body B to guide a surgical tool, a camera, and/or a lighting therein. The buckling prevention device 1 may assist in stably sliding of the overtube T in the longitudinal direction without bending deformation. The overtube T may slide forward or backward along the endoscope body B. A plurality of supports 11 may support the plurality of points spaced apart in the longitudinal direction of the overtube T, to prevent buckling from occurring in the overtube T. In particular, the above buckling prevention device 1 may be necessary for an endoscopic operation.

The buckling prevention device 1 may include the plurality of supports 11 configured to support the overtube T, a base 12 configured to support the plurality of supports 11, and a wire including elastic bodies El, E2, and E3 provided between two neighboring supports among the plurality of supports 11.

The plurality of supports 11 may include an endoscope support 111, an overtube support 112, and one or more additional supports 113 and 114. Although two additional supports, for example, the additional supports 113 and 114, are illustrated in the drawings, a number of additional supports is not limited thereto. It should be noted that the overtube support 112, the first additional support 113, and the second additional support 114 may also be referred to as a first support, a second support, and a third support, respectively.

The endoscope support 111 may support the endoscope body B, and may support a portion of the overtube T most adjacent to the endoscope body B, in comparison to the other supports. The endoscope support 111 may be integrally formed with the endoscope body B to be slidable along the base 12. The endoscope support 111 may be installed to slidably move along a guide member, for example, a rail provided in the base 12. For example, the endoscope body B may be detached from or attached to the endoscope support 111.

The overtube support 112 may be provided on a side opposite to the endoscope support 111 based on the additional supports 113 and 114, and may support a portion of the overtube T spaced the farthest apart from the endoscope body B in comparison to the other supports. The overtube support 112 may protrude upwards from the base 12. The overtube support 112 may remain fixed to the support 12.

The one or more additional supports 113 and 114 may be provided between the endoscope support 111 and the overtube support 112. The one or more additional supports 113 and 114 may be installed slidably with respect to the base 12 and may support the overtube T. The one or more additional supports 113 and 114 may prevent buckling from occurring in the overtube T between the endoscope support 111 and the overtube support 112.

The elastic bodies E1, E2, and E3 may be provided between two neighboring supports among a plurality of supports. For example, the first elastic body E1 may be provided between the overtube support 112 and the first additional support 113, the second elastic body E2 may be provided between the first additional support 113 and the second additional support 114, and the third elastic body E3 may be provided between the second additional support 114 and the endoscope support 111. The elastic bodies E1, E2, and E3 may be compressed or extended based on a sliding distance of the endoscope support 111.

As shown in the drawings, when one elastic body is provided between each pair of supports that are most adjacent to each other, an elastic modulus of each elastic body may be the same. Based on the above configuration, a distance between a pair of supports that are most adjacent to each other among the plurality of supports may equally change in proportion to a movement distance of the endoscope support 111. Meanwhile, unlike the drawings, a plurality of elastic bodies may also be included in parallel or in series between each pair of supports. In this case, a plurality of elastic bodies included between each pair of supports may have the same elastic modulus (i.e., equivalent elastic moduli).

For example, when the elastic bodies E1, E2, and E3 have the same elastic modulus, and when a stroke length of the endoscope body B is denoted by D, an amount of deformation of each of the elastic bodies E1, E2, and E3 may be equal to D/3.

Meanwhile, due to the structure shown in FIGS. 1 and 2, a distance between a pair of supports that are most adjacent to each other may be inevitably at least greater than a length of each of the elastic bodies E1, E2, and E3. In other words, a total length of the base 12 may be inevitably increased by a length of each of the elastic bodies E1, E2, and E3. In addition, if a relatively short elastic body is used, the above problem may be reduced, however, a physical limitation may be present. Furthermore, since an elastic limit is typically proportional to an initial length of an elastic body, an elastic body having a sufficiently long initial length may need to be used to secure a sufficient stroke distance. Considering the above circumstances, when 0.75 m is required as a stroke distance of the endoscope body B, at least 1.5 m is required as the total length of the base 12 based on the structure shown in FIGS. 1 and 2. If the length of the base 12 increases as described above, a wider space occupied by all surgical equipment may be required, which may cause a problem. To dramatically reduce the above problem, another embodiment will be described below.

Figure 3:
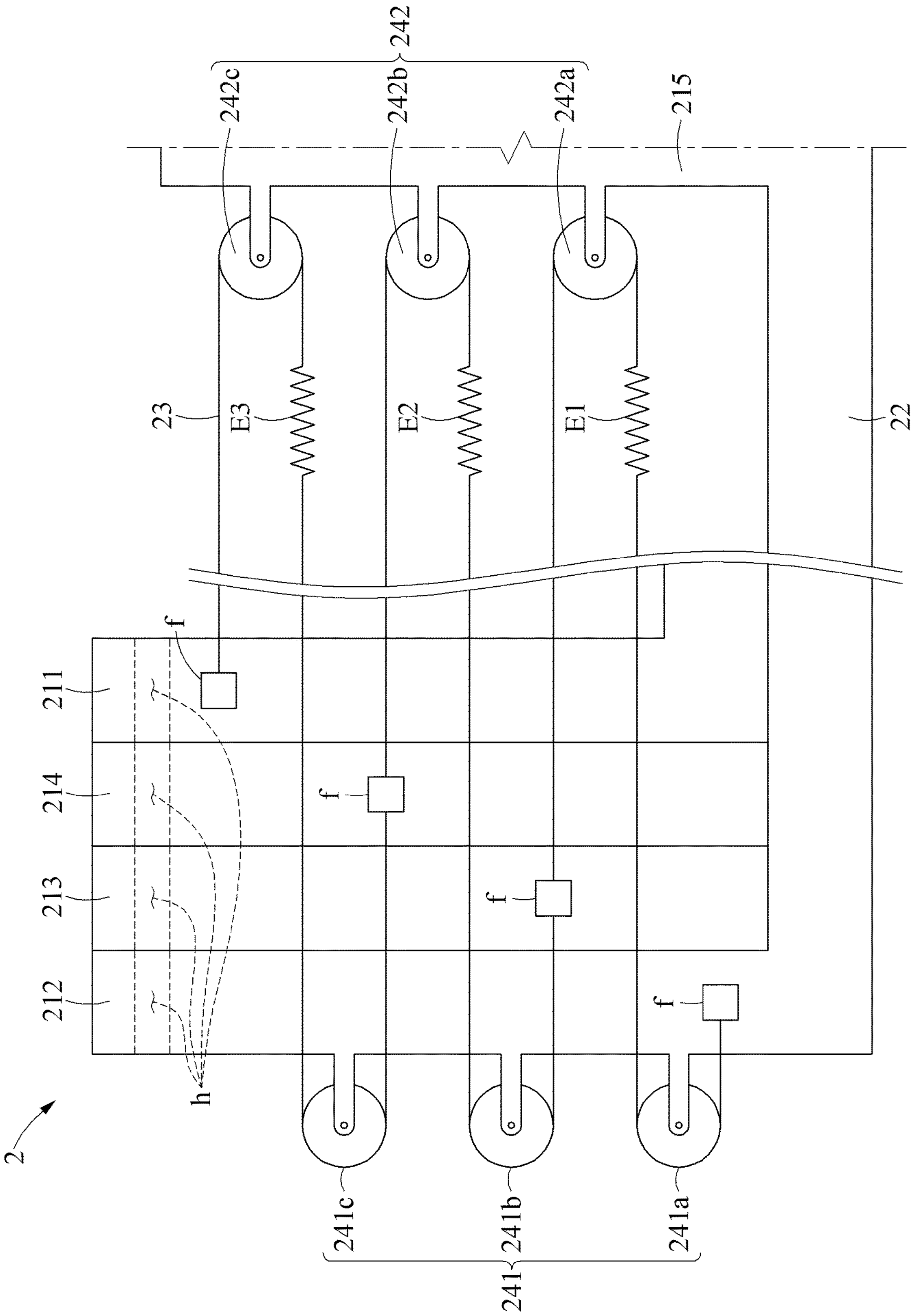
FIG. 3 is a diagram schematically illustrating a buckling prevention device for an endoscope overtube according to an embodiment.
Figure 4:
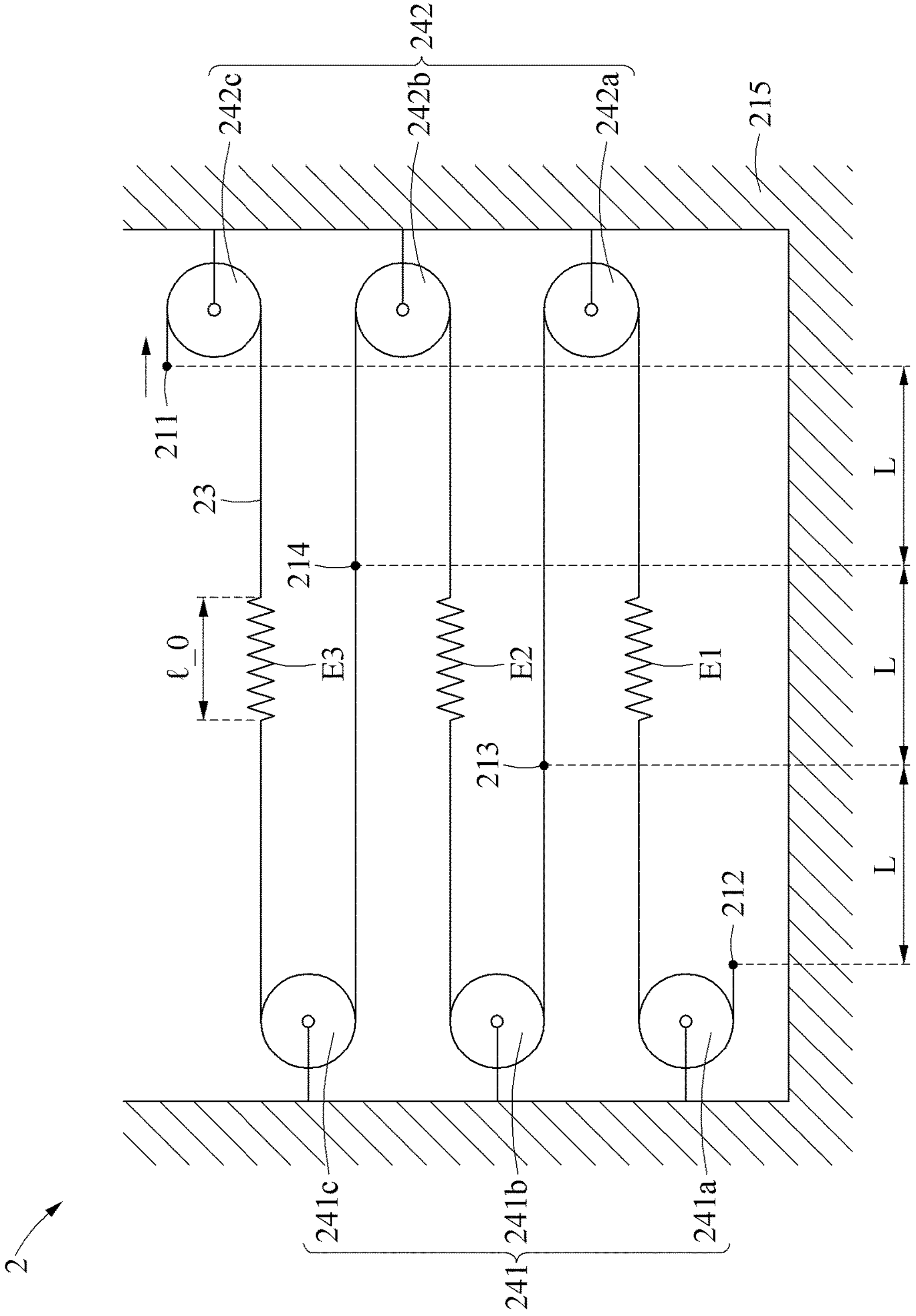
FIG. 4 is a diagram illustrating a state in which a buckling prevention device for an endoscope overtube according to an embodiment is maximally extended.

FIG. 3 is a diagram schematically illustrating a buckling prevention device for an endoscope overtube according to an embodiment. FIG. 4 is a diagram illustrating a state in which a buckling prevention device for an endoscope overtube according to an embodiment is maximally extended, and FIG. 5 is a diagram illustrating a state in which a buckling prevention device for an endoscope overtube according to an embodiment is maximally compressed.

Figure 5:
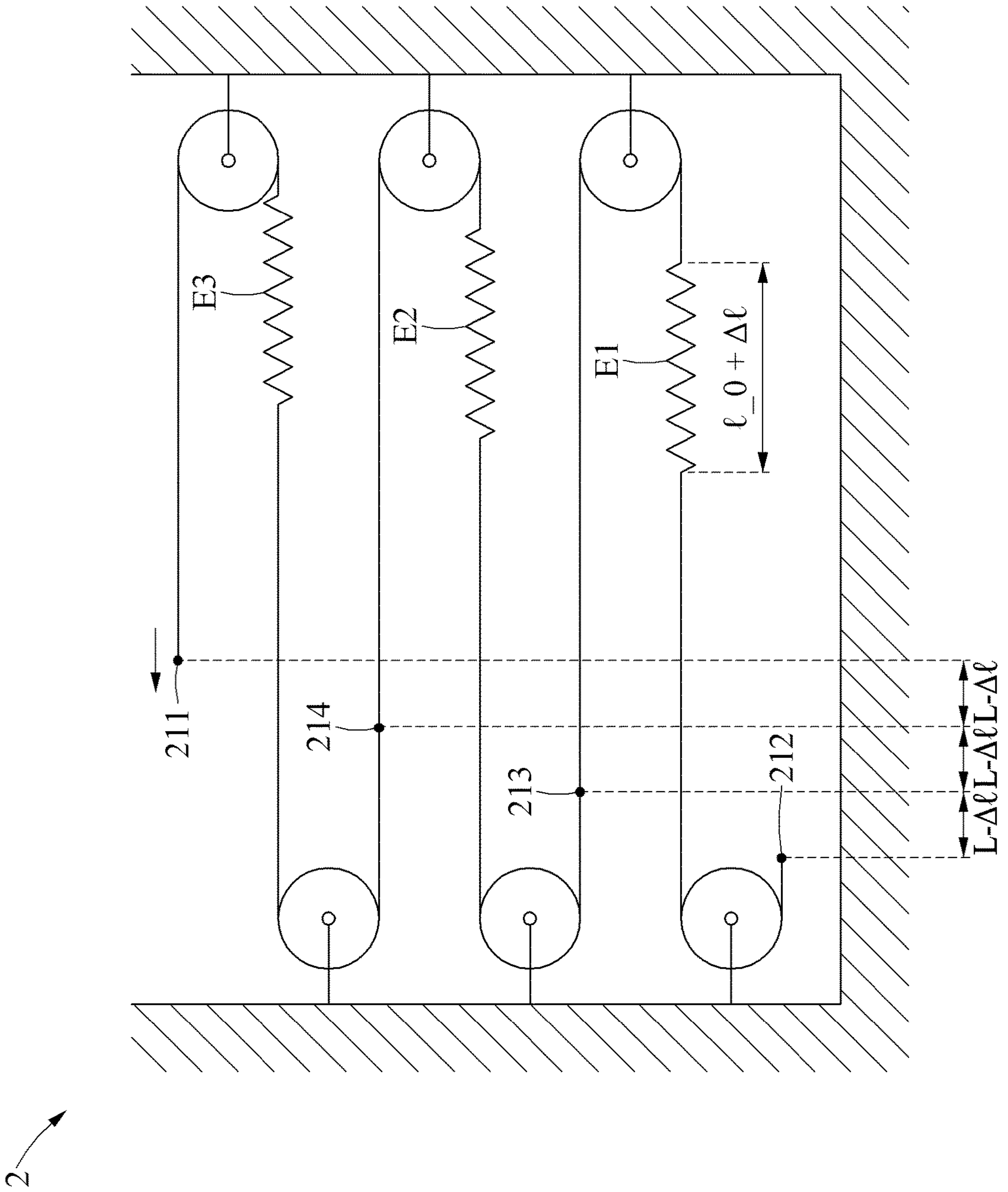
FIG. 5 is a diagram illustrating a state in which a buckling prevention device for an endoscope overtube according to an embodiment is maximally compressed.

Referring to FIGS. 3 through 5, a buckling prevention device 2 may include an endoscope support 211, an overtube support 212, additional supports 213 and 214, a rear wall portion 215, a base 22, a wire 23, which includes a plurality of elastic bodies E1, E2, and E3, a plurality of first hook portions 241, and a plurality of second hook portions 242. The first hook portions 241 and the second hook portions 242 may also be collectively referred to as hook portions.

The buckling prevention device 2 of FIGS. 3 through 5 may provide a structure in which two neighboring supports among the plurality of supports 211, 212, 213, and 214 come in close contact with each other, regardless of an initial length of an elastic body, and thus the buckling prevention device 2 may be configured to have a compact length while ensuring a desired stroke length.

The endoscope support 211 may be slidably connected to the base 22. The endoscope support 211 may move integrally with an endoscope body (not shown) in a state of supporting the endoscope body. The endoscope body may be detached from or attached to the endoscope support 211.

The overtube support 212 may protrude upwards from a front portion of the base 22. The overtube support 212 may be fixed to the base 22. The overtube support 212 may also be understood as a portion of the base 22.

The additional supports 213 and 214 may be installed slidably with respect to the base 22, between the endoscope support 211 and the overtube support 212.

Each of the plurality of supports 211, 212, 213, and 214 may include a support hole h to support an overtube T. The support hole h of each of the plurality of supports 211, 212, 213, and 214 may be formed at the same height from the base 22 to support the overtube T at the same height. An overtube (not shown) may pass through the support hole h.

Based on a sliding operation of the endoscope support 211, spacings between each pair of supports that are most adjacent to each other among a plurality of supports may change, and variations in the spacings may be identical to each other. For example, when the endoscope support 211 moves backward, a spacing between the additional support 213 and the additional support 214 and a spacing between the overtube support 212 and the additional support 213 may increase by a mechanism that will be described below, in addition to a spacing between the endoscope support 211 and the additional support 214. In addition, variations in spacings between each pair of supports that are most adjacent to each other among a plurality of supports may be identical to each other.

The rear wall portion 215, which is a portion fixed to the base 22, may be provided behind the endoscope support 211 in a state of being spaced apart from the endoscope support 211, and may support a second hook portion 242 that will be described below. The rear wall portion 215 may be understood as a portion of the base 22.

The base 22 may support the plurality of supports.

The wire 23 may be fixed to each of the plurality of supports based on an arrangement order from the overtube support 212 to the endoscope support 211. For example, a first point, a second point, a third point, and a fourth point of the wire 23 may be fixed to the overtube support 212, the first additional support 213, the second additional support 214, and the endoscope support 211, respectively. The plurality of supports may each include a fixing portion f to fix the wire 23.

The wire 23 may be disposed to be bent a plurality of times from one end to another end. For example, the wire 23 may be bent twice between the first point and the second point, between the second point and the third point, and between the third point and the fourth point, respectively. The wire 23 may be bent six times in total from the first point to the fourth point.

As shown in the drawings, a wire may be bent twice between a pair of fixing portions that are most adjacent to each other, and accordingly a pair of supports that are most adjacent to each other may move in the same direction (an upstream direction or a downstream direction). Meanwhile, unlike the drawing, it should be noted that the wire does not necessarily need to have a shape bent twice between a pair of fixing portions that are most adjacent to each other, and that it is sufficient to have a shape bent an even number of times. In other words, an even number of hook portions may be arranged between a pair of fixing portions that are most adjacent to each other.

The wire 23 may include the plurality of elastic bodies E1, E2, and E3 to allow a total length of the wire 23 to be changed based on a sliding distance of the endoscope support 211. For example, a state in which the plurality of elastic bodies E1, E2, and E3 are extended may be shown in FIG. 3, and the extended length of the plurality of elastic bodies E1, E2, and E3 may gradually decrease while the endoscope support 211 is moving toward the rear wall portion 215.

For example, each of the plurality of elastic bodies E1, E2, and E3 may provide an elastic force in a direction in which the endoscope support 211 moves away from the overtube support 212. If an external force is not applied due to the plurality of elastic bodies E1, E2, and E3, the endoscope support 211 may return to a default position (refer to FIG. 4).

For example, the plurality of elastic bodies E1, E2, and E3 may have the same elastic modulus. As shown in the drawings, if one elastic body is included between a pair of supports that are most adjacent to each other, respective elastic bodies may have the same elastic modulus. Based on the above configuration, a distance between the plurality of supports may equally change. Meanwhile, unlike the drawings, a plurality of elastic bodies may also be included in series or in parallel between a pair of supports. In this case, a plurality of elastic bodies included between each pair of supports may have the same elastic modulus (i.e., equivalent elastic moduli).

Based on a sliding operation of the endoscope support 211, variations in spacings between each pair of supports that are most adjacent to each other among the plurality of supports may be identical to each other. In other words, based on the sliding operation of the endoscope support 211, a displacement amount by which the second additional support 214 slides may be greater than a displacement amount by which the first additional support 213 slides.

The plurality of first hook portions 241 and the plurality of second hook portions 242 may support the wire 23 such that the wire 23 may remain bent. The wire 23 may be caught once in each of a first hook portion and a second hook portion between two neighboring points among the first point to the fourth point. For example, at least a part of the plurality of hook portions may be a pulley that is rotatably installed at a specific position with respect to the base 22 so that the wire 23 may be smoothly driven.

For example, the plurality of first hook portions 241 may be installed in the overtube support 212, and the plurality of second hook portions 242 may be installed in the rear wall portion 215. For example, a plurality of first hook portions 241*a*, 241*b*, and 241*c* may be spaced apart from each other in a height direction of the overtube support 212, and a plurality of second hook portions 242*a*, 242*b*, and 242*c* may be spaced apart from each other in a height direction of the rear wall portion 215.

Meanwhile, it should be noted that a position in which each hook portion is installed is not limited to those shown in FIG. 3. It will be understood by one of ordinary skill in the art that each hook portion does not need to be installed in the overtube support 212 or the rear wall portion 215 and that it is sufficient that each hook portion is installed at a specific position with respect to the base 22 as shown in FIGS. 4 and 5 that will be described below. It is clearly noted that other embodiments utilizing the principle shown in the present embodiment are also included in the scope of the right of the present patent.

A driving mechanism of the buckling prevention device 2 will be described with reference to FIGS. 4 and 5. In FIGS. 4 and 5, a fixing portion of each of the plurality of supports 211, 212, 213, and 214 is indicated by a dot.

First, FIG. 4 shows an example in which the buckling prevention device 2 is in a default position. If an external force is not applied to the endoscope support 211, the endoscope support 211 may be maintained in a position shown in FIG. 4. In the default position, a distance between the endoscope support 211 and the second additional support 214, a distance between two additional supports 213 and 214, and a distance between the overtube support 212 and the first additional support 213 may be the same, for example, L. Each of the plurality of elastic bodies E1, E2, and E3 may have a length l_0. The wire 23 may be provided in a state of being caught in the plurality of first hook portions 241 and the second hook portions 242 in a crossing manner.

Next, FIG. 5 illustrates an example in which the endoscope support 211 moves forward in the state of FIG. 4. If the endoscope support 211 moves forward and a length of each of the elastic bodies E1, E2, and E3 increases to "l_0+Δl", a distance between two neighboring supports among the plurality of supports 211, 212, 213, and 214 may be reduced to "L-Δl". In this example, the endoscope support 211 may move by a distance of 3Δl, the additional support 214 may move by a distance of 2Δl, and the additional support 213 may move by a distance of Δl. As a result, a distance between a pair of supports that are adjacent to each other may be equally changed so that the overtube T may be supported at an even position, to effectively prevent buckling from occurring in the overtube T.

Figure 6:
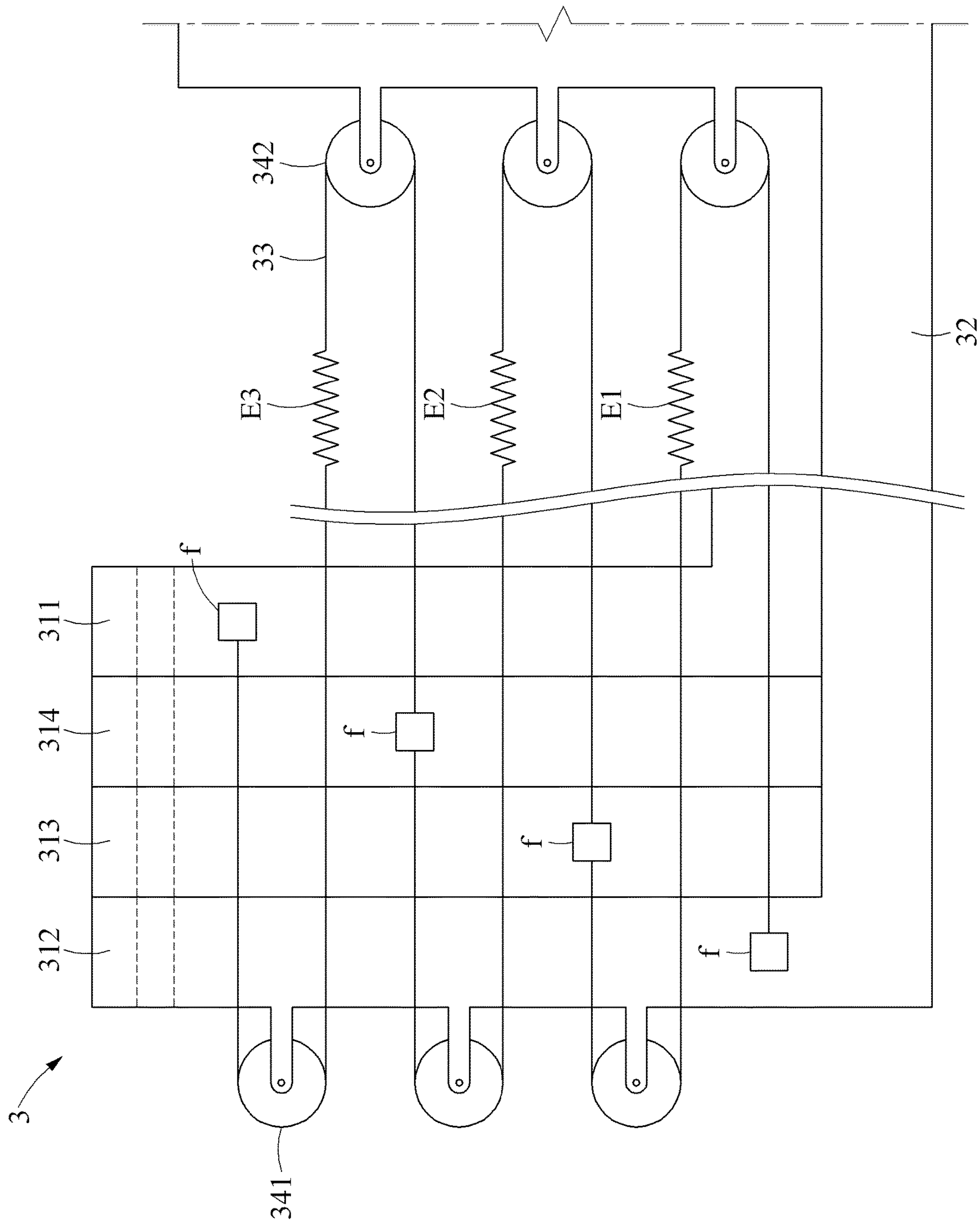
FIG. 6 is a diagram schematically illustrating a buckling prevention device for an endoscope overtube according to an embodiment.

FIG. 6 is a diagram schematically illustrating a buckling prevention device for an endoscope overtube according to an embodiment. FIG. 6 illustrates an example in which a wire 33 is connected along a path different to that of FIG. 3, and operational characteristics are the same.

Referring to FIG. 6, a buckling prevention device 3 may include an endoscope support 311, an overtube support 312, additional supports 313 and 314, a base 32, a wire 33, a plurality of first hook portions 341, and a plurality of second hook portions 342. The wire 33 may be caught in a plurality of hook portions in a direction opposite to a direction in which the wire 23 of FIG. 3 is caught. For example, the wire 33 of the buckling prevention device 3 may be caught sequentially in the second hook portions 342 and the first hook portions 341, based on a direction from a first point toward a second point.

While the embodiments are described with reference to drawings, it will be apparent to one of ordinary skill in the art that various alterations and modifications in form and details may be made in these embodiments without departing from the spirit and scope of the claims and their equivalents. For example, suitable results may be achieved if the described techniques are performed in a different order, and/or if components in a described system, architecture, device, or circuit are combined in a different manner, and/or replaced or supplemented by other components or their equivalents.

The invention claimed is:

1. A buckling prevention device for an endoscope overtube, the buckling prevention device comprising:
- a plurality of supports configured to support an endoscope overtube; and
- a base configured to support the plurality of supports,
- wherein the plurality of supports comprises:
- an endoscope support slidably connected to the base and configured to support an endoscope body;
- an overtube support fixed to one side of the base and configured to support an overtube connected to the endoscope body; and
- at least one additional support configured to support the overtube, the at least one additional support being installed slidably with respect to the base, between the endoscope support and the overtube support, and
- wherein the buckling prevention device further comprising:
- a first elastic wire having a first length connecting the endoscope support to the at least one additional support,
- a second elastic wire having a second length connecting the overtube support to the at least one additional support,
- a sum of the first length and second length defines a third length,
- wherein sliding of the endoscope support along the base changes the third length while the first length remains equivalent to the second length,
- wherein each of the first elastic wire and the second elastic wire is disposed to be bent a plurality of times from one end to another end.

2. The buckling prevention device of claim 1, wherein the first elastic wire and the second elastic wire are configured to provide elastic forces in a direction in which the endoscope support moves away from the overtube support.

3. The buckling prevention device of claim 1, wherein the first elastic wire and the second elastic wire have a same equivalent elastic modulus.

4. The buckling prevention device of claim 1, wherein the endoscope body is detachable from the endoscope support.

* * * * *